(12) United States Patent
Kaneda

(10) Patent No.: US 11,337,704 B2
(45) Date of Patent: May 24, 2022

(54) TOOL FOR TREATING EXCISED END OF BODY ORGAN

(71) Applicant: JICHI MEDICAL UNIVERSITY, Tokyo (JP)

(72) Inventor: Yuji Kaneda, Shimotsuke (JP)

(73) Assignee: JICHI MEDICAL UNIVERSITY, Tokyo (JP)

( * ) Notice: Subject to any disclaimer, the term of this patent is extended or adjusted under 35 U.S.C. 154(b) by 0 days.

(21) Appl. No.: 16/641,623

(22) PCT Filed: Aug. 24, 2018

(86) PCT No.: PCT/JP2018/031328
§ 371 (c)(1),
(2) Date: Feb. 24, 2020

(87) PCT Pub. No.: WO2019/039586
PCT Pub. Date: Feb. 28, 2019

(65) Prior Publication Data
US 2021/0161534 A1 Jun. 3, 2021

(30) Foreign Application Priority Data
Aug. 24, 2017 (JP) .............................. JP2017-161201

(51) Int. Cl.
*A61B 17/12* (2006.01)
(52) U.S. Cl.
CPC ................... *A61B 17/12009* (2013.01); *A61B 2017/12004* (2013.01)
(58) Field of Classification Search
CPC .... A61B 17/12009; A61B 2017/12004; A61B 17/12; A61B 17/12013; A61B 17/122; A61B 17/132
See application file for complete search history.

(56) References Cited

U.S. PATENT DOCUMENTS 5,203,786 A 4/1993 Vernick
5,649,937 A 7/1997 Bito et al.
(Continued)

FOREIGN PATENT DOCUMENTS

EP 3146917 A2 3/2017
JP S57-150605 U 9/1982
(Continued)

OTHER PUBLICATIONS

International Preliminary Examination Report (with partial English explanation) dated Feb. 25, 2020 for Application No. PCT/JP2018/031328.
(Continued)

*Primary Examiner* — Melanie R Tyson
(74) *Attorney, Agent, or Firm* — Fay Sharpe LLP

(57) ABSTRACT

This tool is for treating an excised end of a body organ and is provided with: a long and thin, flexible first band section having a distal end and a proximal end that are made of a biodegradable-absorptive polymer; a long and thin, flexible second band section having a distal end and a proximal end that are made of a biodegradable-absorptive polymer; and a first locking section having a first ratchet claw made of a biodegradable-absorptive polymer, wherein the first locking section is formed at the distal end of the second band section, the distal end of the first band section and the proximal end of the second band section are joined together, at least one ratchet tooth that is capable of meshing with the first ratchet claw is formed on the external surface of the first band section, and the engagement of the ratchet tooth with the first ratchet claw forms a flattened ring which is used to bind a body organ so as to ligate a tube or cavity that opens at an excised end of the body organ.

17 Claims, 20 Drawing Sheets

(56) References Cited

U.S. PATENT DOCUMENTS

| | | | |
|---|---|---|---|
| 5,741,283 A * | 4/1998 | Fahy | A61B 17/0057 |
| | | | 606/157 |
| 9,066,721 B2 | 6/2015 | Ichihara et al. | |
| 9,730,699 B2 | 8/2017 | Höglund | |
| 2004/0032332 A1 | 2/2004 | Schiebler | |
| 2006/0264987 A1 | 11/2006 | Sgro | |
| 2007/0265644 A1 | 11/2007 | Ichihara et al. | |
| 2010/0234862 A1 * | 9/2010 | Patel | A61B 17/12009 |
| | | | 606/151 |
| 2014/0012293 A1 | 1/2014 | Bertolero et al. | |
| 2015/0157327 A1 | 6/2015 | Höglund | |

FOREIGN PATENT DOCUMENTS

| | | |
|---|---|---|
| JP | H05-337123 A | 12/1993 |
| JP | 2004298501 A | 10/2004 |
| JP | 2006087671 A | 4/2006 |
| JP | 2015-523144 A | 8/2015 |

OTHER PUBLICATIONS

Nogami, "Study on Treatment of Pancreatic Stump in splenectomy and pancreatectomy," Chiba Medical Journal, vol. 32, first issue, pp. 108-113, Date unknown.
Nogami, "Study on Treatment of Pancreatic Stump in splenectomy and pancreatectomy," Chiba Medical Journal, vol. 32, first issue, pp. 108-113, Publication Date = 1956.
International Search Report (with English translation) dated Nov. 6, 2018 for Application No. PCT/JP2018/031328.
Written Opinion (with English translation) dated Nov. 6, 2018 for Application No. PCT/JP2018/031328.
Supplementary Partial European Search for European Patent Patent Application No. 18849290.4, dated Feb. 17, 2021, 11 pages.

* cited by examiner

2

3

3

3

25

TOOL FOR TREATING EXCISED END OF BODY ORGAN

TECHNICAL FIELD

The present invention relates to an organ stump treatment tool. More specifically, the present invention relates to an organ stump treatment tool with less invasion and for preventing the occurrence of various types of complications in partial resection of an organ such as a liver or a pancreas.

BACKGROUND ART

Hepatectomy or pancreatectomy has been known as an effective treatment method for liver tumors or pancreatic tumors. A pancreas is composed of three parts including a pancreatic head, a pancreatic body, and a pancreatic tail. The pancreatic head contacts a duodenum. The pancreatic tail contacts a spleen. For resection of the pancreatic body or pancreatic tail, an instrument called an autosuture device is used for a treatment of dissecting the pancreas and closing a stump thereof simultaneously, for example. After implementation of the resection using the autosuture device, however, the closure of the stump is released in a high ratio to cause a pancreatic fistula. Additionally, as the resection using the autosuture device involves many staples passed through a pancreatic parenchymal cell for closing the stump, making pancreatic parenchymal injury or pancreatic duct injury unavoidable.

Non-Patent Document 1 cites the following as treatment methods to be performed after resection of a pancreatic tail: a method comprising cutting a stump into a wedge shape, ligating a pancreatic duct and closing and suturing the stump so as to join wound surfaces (fish-mouth method); a method comprising binding an entire circumference of a stump of pancreas with a ligature thread (mass-ligation method); and a method comprising ligating a pancreatic duct and then covering a cross section with a serous membrane or a caul. In addition to these methods, there are known methods including a method comprising dissecting a small-intestinal wall and suturing and covering a pancreatic stump with the small-intestinal wall, a method comprising affixing a non-woven fabric made of polyglycolic acid with a fibrin adhesive, etc. Among these methods, the mass-ligation method does not involve use of needles or staples and is free from invasion due to passage of needles or staples. Thus, this method is expected to achieve the effect of reducing the frequency of the occurrence of pancreatic fistulas. In this method, however, it is difficult to control tension during tight binding and the tight binding may be loosened during ligation. Additionally, as a ligature thread at a pancreatic surface digs into a pancreatic parenchymal cell, a pancreatic coating or the pancreatic parenchymal cell may be injured.

Various types of medical devices for ligation have been suggested. For example, Patent Document 1 discloses a ligature band comprising a tourniquet body of a predetermined length. Retention interlocking parts are formed continuously within a range corresponding to an interference in the lengthwise direction of the tourniquet body. Non-slip ribs are formed continuously at appropriate positions of the tourniquet body over a range where the retention interlocking parts are formed. Further, the tourniquet body has a base end where a buckle portion is formed integrally. The buckle portion is formed into a short tunnel-like shape with an insertion opening formed on one side and a feeder opening formed on the other side, and has an engagement hook formed at an appropriate inner position and usable for engaging the retention interlocking parts of the tourniquet body fed in from the tip in a manner preventing the retention interlocking parts from coming off. The ligature band is made of a synthetic resin formed article having flexibility in its entirety. Cited Document 1 states that a biodegradable synthetic resin is applicable.

Patent Document 2 discloses a medical device for tissue ligation comprising: an elongated, flexible band having a front side, a rear side, a leading end and a trailing end, and having perforations and rungs defined therein; a locking case connected to the trailing end of the band and having a channel dimensioned for reception of the band; and a locking member connected to the locking case and disposed in connection with the channel and configured to interlock perforations and rungs defined in the band. The channel in the locking case comprises an arching portion arranged opposite to the locking member. The band is configured to arch over the locking member and protruded at least partly into the arching portion when the locking member engages a rung of the band. Patent Document 2 states that the medical device is at least partly made of a polymer selected from a group consisting of polyglycolide, poly-L-lactide, poly-p-dioxanone, poly(trimethylene carbonate), polycaprolactone and co-polymers derived from two or more monomers selected from a group consisting of glycolide, L-lactide, p-dioxanone, trimethylene carbonate and ε-caprolactone.

CITATION LIST

Patent Literatures

Patent Document 1: JP 2004-298501 A
Patent Document 2: JP 2015-523144 A

Non-Patent Literature

Non-Patent Document 1: Nogami, "Study on Treatment of Pancreatic Stump in splenectomy and pancreatectomy," Chiba Medical Journal, Vol. 32, First Issue, pp. 108-113

SUMMARY OF THE INVENTION

Problems to be Solved by the Invention

An object of the present invention is to provide an organ stump treatment tool with less invasion for preventing the occurrence of various types of complications in partial resection of an organ such as a liver or a pancreas.

Means for Solving the Problems

Intensive studies for solving the above problems result in completing the present invention including the following embodiments.

[1] An organ stump treatment tool comprising: an elongated flexible band portion having a distal end and a proximal end and made of a biodegradable and bioabsorbable polymer; and a locking portion comprising a second interlocking part and made of a biodegradable and bioabsorbable polymer, wherein the locking portion is formed at the distal end of the band portion, and the band portion comprises a flexed part between the distal end and the proximal end, and comprises a first interlocking part between the flexed part and the proximal end for meshing engagement with the second interlocking part, whereby the meshing engagement of the first interlocking part with the second interlocking part makes a flattened ring having at least one flexed part recessed inwardly, and the flattened ring binds an organ tightly to ligate a duct or lumen that opens at a stump of the organ.

[2] An organ stump treatment tool comprising:
an elongated flexible first band portion having a distal end and a proximal end and made of a biodegradable and bioabsorbable polymer;
an elongated flexible second band portion having a distal end and a proximal end and made of a biodegradable and bioabsorbable polymer; and
a first locking portion comprising a first ratchet pawl and made of a biodegradable and bioabsorbable polymer, wherein the first locking portion is formed at the distal end of the second band portion, the distal end of the first band portion and the proximal end of the second band portion are joined so as to flex the first band portion and the second band portion, and
at least one ratchet tooth capable of being meshed with the first ratchet pawl is formed on the outer surface of the first band portion, whereby meshing engagement of the ratchet tooth with the first ratchet pawl makes a flattened ring having at least one flexed part recessed inwardly, the flattened ring binds an organ tightly to ligate a duct or lumen that opens at a stump of the organ.

[3] The organ stump treatment tool according to [2], wherein at least one of the first band portion and the second band portion has an inner surface where at least one convex strip is formed to extend in a lengthwise direction.

[4] The organ stump treatment tool according to [2] or [3], further comprising a tongue part, formed in the vicinity of the first locking portion, for preventing an organ tissue from getting caught in the organ stump treatment tool.

[5] The organ stump treatment tool according to any one of [2] to [4], wherein the distal end of the first band portion and the proximal end of the second band portion are joined at an angle smaller than a right angle so as to define a nonangular and smooth inner surface.

[6] The organ stump treatment tool according to any one of [2] to [5], further comprising a second locking portion comprising a second ratchet pawl made of a biodegradable and bioabsorbable polymer, wherein
the first ratchet pawl is allowed to be released from meshing engagement with the ratchet tooth even meshed with the first ratchet pawl, and the second ratchet pawl is prohibited from being released from meshing engagement with the ratchet tooth once meshed with the second ratchet pawl.

[7] The organ stump treatment tool according to any one of [2] to [6], wherein the first band portion or the second band portion comprises holes having openings aligned in a lengthwise direction.

[8] The organ stump treatment tool according to any one of [1] to [7], further comprising a covering member made of a biodegradable and bioabsorbable polymer.

Advantageous Effects of the Invention

A conventional band for ligation forms a ring like a perfect circle during ligation. Hence, pressure to an organ having a flattened cross-sectional shape is low at a short-diameter area and high at a large-diameter area. By contrast, as the organ stump treatment tool of the present invention forms a flattened ring, an organ having a flattened cross-sectional shape can be ligated under pressure applied uniformly over the organ entirely, and the likelihood of injury of the organ is reduced. The organ stump treatment tool of the present invention can prevent the occurrence of various types of complications with less invasion in partial resection of an organ such as a liver or a pancreas. The organ stump treatment tool of the present invention can be used for ligation without causing forced deformation of a soft organ such as a pancreas. The organ stump treatment tool of the present invention does not involve insertion of a needle or a medical staple into a pancreatic parenchyma, making pancreatic parenchymal injury or pancreatic duct injury unlikely. The organ stump treatment tool of the present invention can be operated by simple manipulation and is independent of the skill level of an operator. The organ stump treatment tool of the present invention does not involve extra dissection or anastomosis of a digestive tract. As the organ stump treatment tool of the present invention uses a biodegradable and bioabsorbable polymer, it is useful in terms of medical economical aspect. Using the covering member made of a biodegradable and bioabsorbable polymer in combination reduces the risk of infection, which increases the effect of preventing leakage of fluid or blood from an organ.

EMBODIMENTS FOR CARRYING OUT THE INVENTION

An organ stump treatment tool of the present invention comprises a band portion 2, 3, and a locking portion.

The band portion is an elongated flexible strip-shaped member having a distal end and a proximal end and made of a biodegradable and bioabsorbable polymer.

The locking portion 7 comprises a second interlocking part made of a biodegradable and bioabsorbable polymer, and is formed at the distal end of the band portion, preferably so as to protrude from the outer surface of the band portion at the distal end of the band portion.

The band portion comprises a flexed part 4 between the distal end and the proximal end of the band portion, and comprises a first interlocking part 5 between the flexed part and the proximal end for meshing engagement with the second interlocking part. There is one flexed part 4 in the organ stump treatment tool shown in FIG. 1, two or more flexed parts can be placed in the organ stump treatment tool. When two or more flexed parts are placed, the first interlocking part is arranged between the proximal end and the flexed part closest to the proximal end. Preferably, the first interlocking part is arranged on the outer surface of the band portion or a lateral edge of the band portion.

The flexed part is a part inflected to be recessed inwardly, preferably, a part inflected so as to define a non-angular or smooth inner surface on the inward recess. The flexed part may be obtained by being formed into an inflected state by resin forming, by joining the distal end of the first band portion and the proximal end of the second band portion so as to form a flexure, by inflecting a part of a band member with flexibility and then attaching a member for controlling the flexibility to the flexed part, or by being given elasticity lower or higher than the other parts through reducing or increasing the thickness of the band portion. While the band portion has flexibility and thus can be curved freely, the flexibility is preferably lower, namely, elasticity is preferably higher at the flexed part than the other parts of the band portion for maintaining the foregoing shape in the flexed part. The foregoing member for controlling the flexibility is preferably made of a biodegradable and bioabsorbable polymer.

Figure 6:
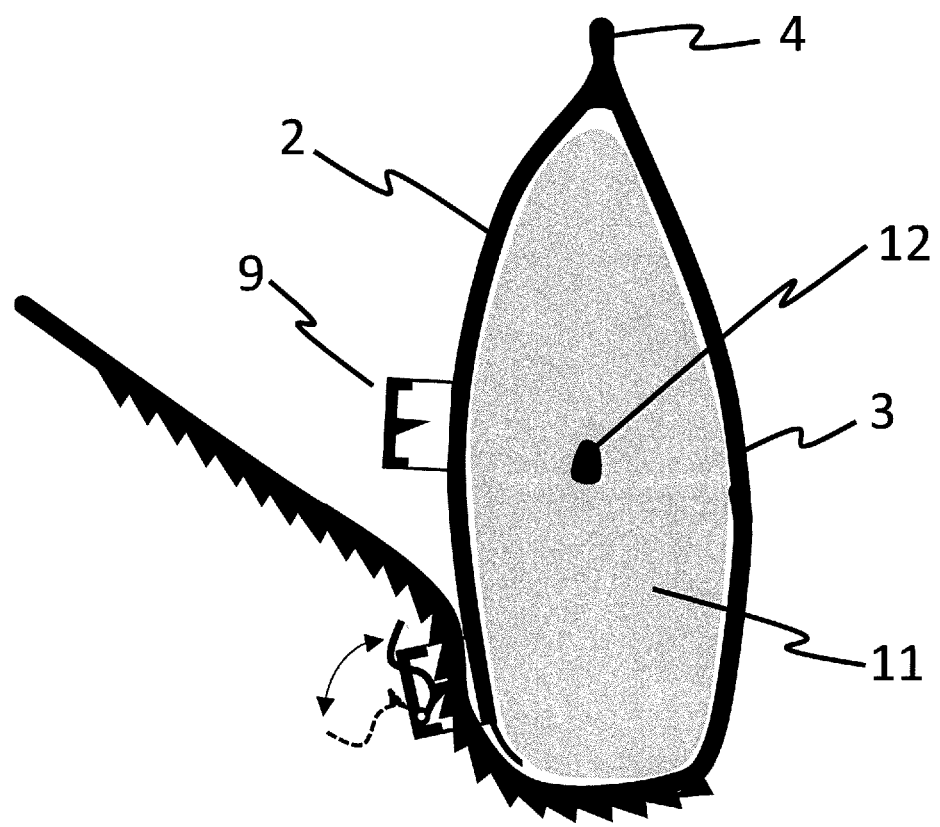
FIG. 6 is a side view showing an example of a state in which the organ stump treatment tool of the present invention is attached to a pancreatic stump.
Figure 7:
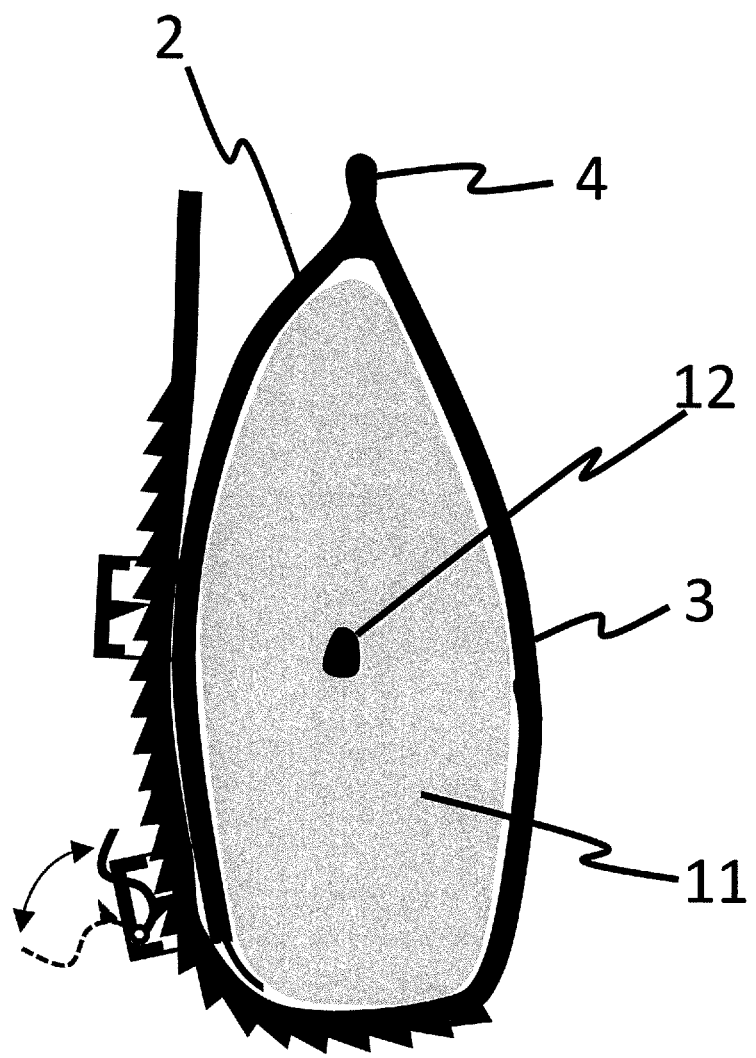
FIG. 7 is a side view showing another example of a state in which the organ stump treatment tool of the present invention is attached to a pancreatic stump.

As long as the first interlocking part and the second interlocking part have respective interlocking shapes corresponding to each other, these interlocking parts are not particularly limited. Examples of the first interlocking part and the second interlocking part include a combination of a plurality of ratchet teeth formed at the outer surface of the band portion and at least one ratchet pawl formed at the locking portion, a combination of a plurality of ratchet teeth formed at the right and left lateral edges of the band portion and at least one pair of right and left ratchet pawls formed at the locking portion, and a combination of a plurality of holes formed at the band portion and a pin formed at the locking portion. The first interlocking part and the second interlocking part can be meshed with each other in such a manner that the inner surface of the band portion 3 contacts the outer surface of the band portion 2 and the proximal end of the band portion 3 is pointed from the distal end toward the proximal end of the band portion 2 (FIG. 6).

When the first interlocking part and the second interlocking part are meshed with each other, the organ stump treatment tool of the present invention forms a flattened ring with at least one flexed part 4 recessed inwardly, and can be used for binding an organ tightly and ligating a duct or lumen that opens at a stump of the organ with the ring. The flattened ring can be used for ligating an organ of a flattened cross-sectional shape entirely with uniform pressure and is unlikely to injure the organ.

The organ stump treatment tool of the present invention is made of a biodegradable and bioabsorbable polymer. Examples of the biodegradable and bioabsorbable polymer can include lactic acid polymers, lactic acid-glycolic acid polymers, trimethylene carbonate polymers, dioxanone polymers, polyethylene glycol polymers, and lactone polymers. Among these polymers, dioxanone polymers are preferable. The organ stump treatment tool of the present invention can be obtained by processing a biodegradable and bioabsorbable polymer into the shapes of corresponding parts through a known resin shaping method.

Figure 1:
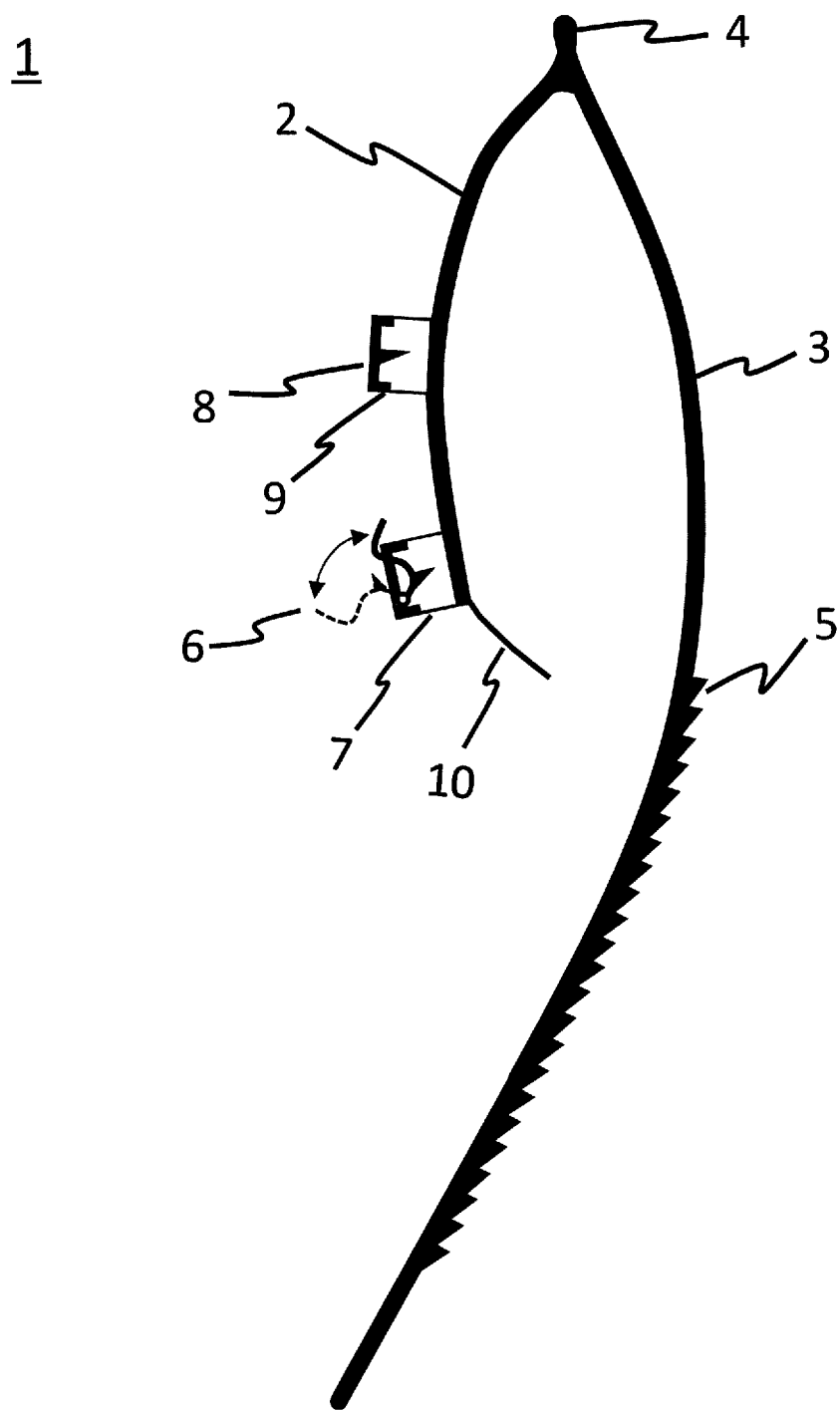
FIG. 1 is a side view showing an example of an organ stump treatment tool of the present invention.

An embodiment of the present invention will be described next by referring to the drawings. An organ stump treatment tool 1 of the present invention comprises a first band portion 3, a second band portion 2, and a first locking portion 7 (FIG. 1).

The first band portion 3 and the second band portion 2 are each an elongated flexible strip-shaped member having a distal end and a proximal end and made of a biodegradable and bioabsorbable polymer.

The first band portion 3 and the second band portion 2 are joined at the distal end of the first band portion 3 and the proximal end of the second band portion 2. A joint 4 may be formed by fusion bonding, adhesive bonding, or axially attaching, for example. Alternatively, the joint 4 may be formed by resin shaping integrally with a shape with the first band portion 3 and the second band portion 2 joined to each other. The distal end of the first band portion 3 and the proximal end of the second band portion 2 are joined so as to inflect the first band portion and the second band portion. In addition to the foregoing formation methods, the flexed joint may be formed by plastically deforming a straight band without a flex made of a biodegradable and bioabsorbable polymer through application of heat, for example. The inner surface of the joint 4 is preferably a non-angular and smooth surface. The non-angular and smooth surface contributes to ligation of an organ entirely with uniform pressure and can reduce the risk of injury of a surface of the organ. Favorably, the first band portion 3 and the second band portion 2 are joined in such a manner that a long axis direction of the first band portion 3 and a long axis direction of the second band portion 2 intersect each other at an angle smaller than a right angle for binding an organ having a flattened shape such as a pancreas, for example.

The first locking portion 7 is formed at the distal end of the second band portion 2. A casing of the first locking portion 7 is preferably made of a biodegradable and bioabsorbable polymer. The first locking portion 7 comprises at least a first ratchet pawl 6 made of a biodegradable and bioabsorbable polymer.

Figure 2:
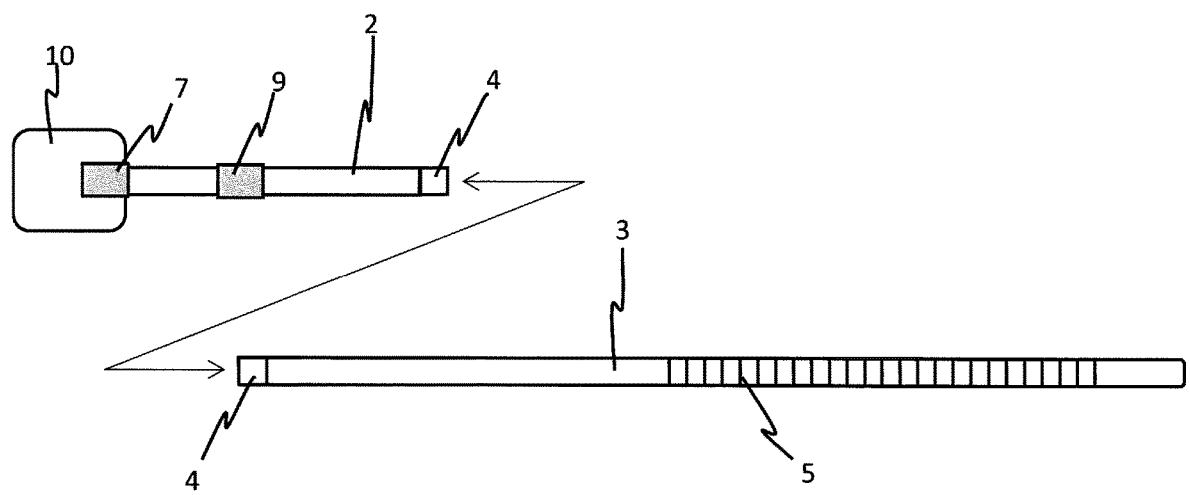
FIG. 2 shows the outer surface of the organ stump treatment tool in FIG. 1 in a developed state.
Figure 3:
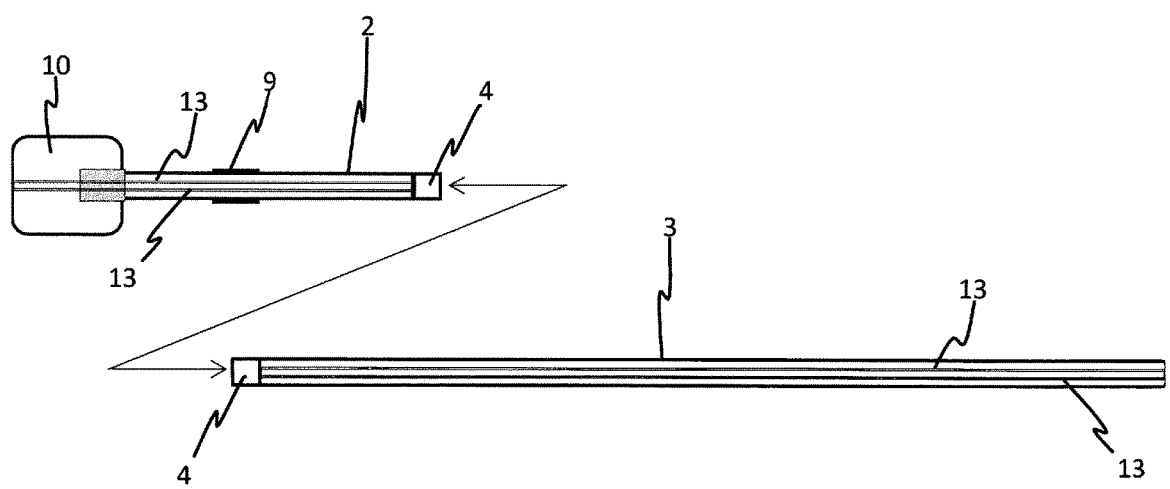
FIG. 3 shows the inner surface of the organ stump treatment tool in FIG. 1 in a developed state.
Figure 4:
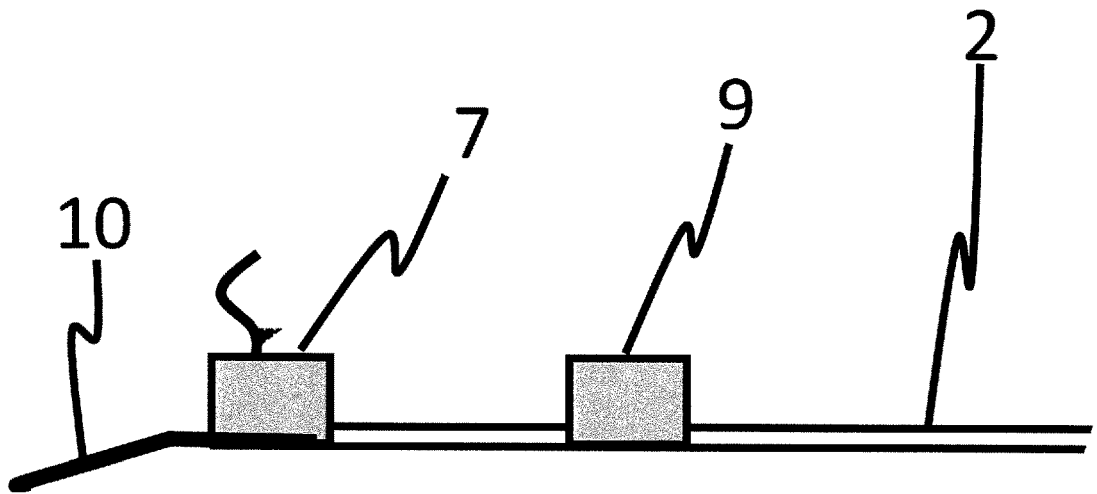
FIG. 4 shows the side surfaces of a tongue part and a second band portion of the organ stump treatment tool in FIG. 1.
Figure 11:
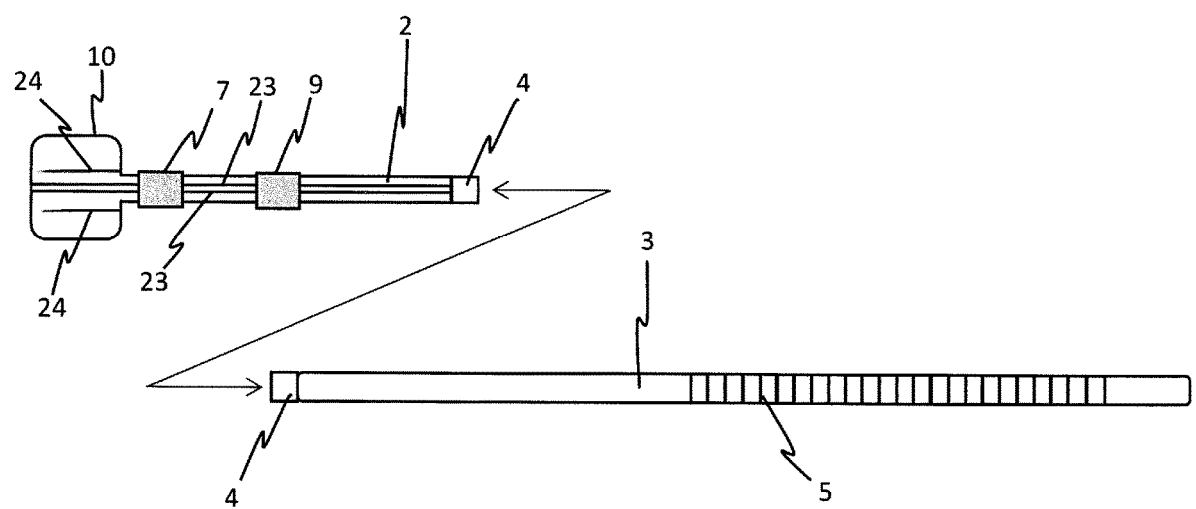
FIG. 11 shows the outer surface of an example of the organ stump treatment tool of the present invention in a developed state.
Figure 12:
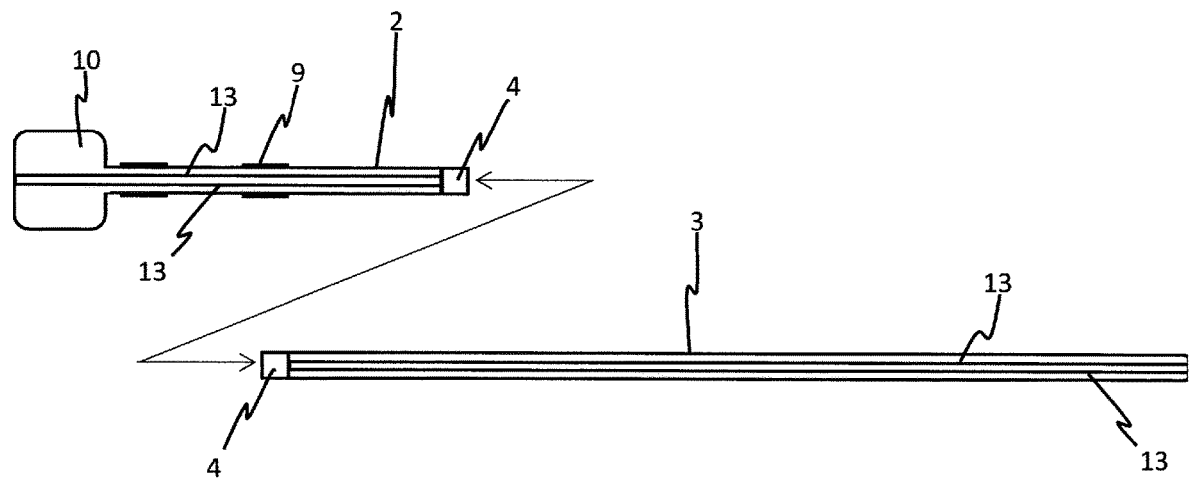
FIG. 12 shows the inner surface of the organ stump treatment tool in FIG. 11 in a developed state.
Figure 13:
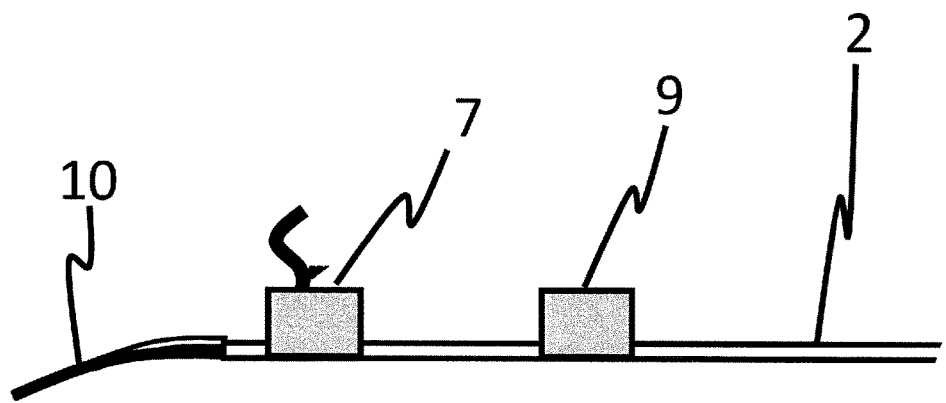
FIG. 13 shows side surfaces of a tongue part and a second band portion of the organ stump treatment tool in FIG. 11.
Figure 14:
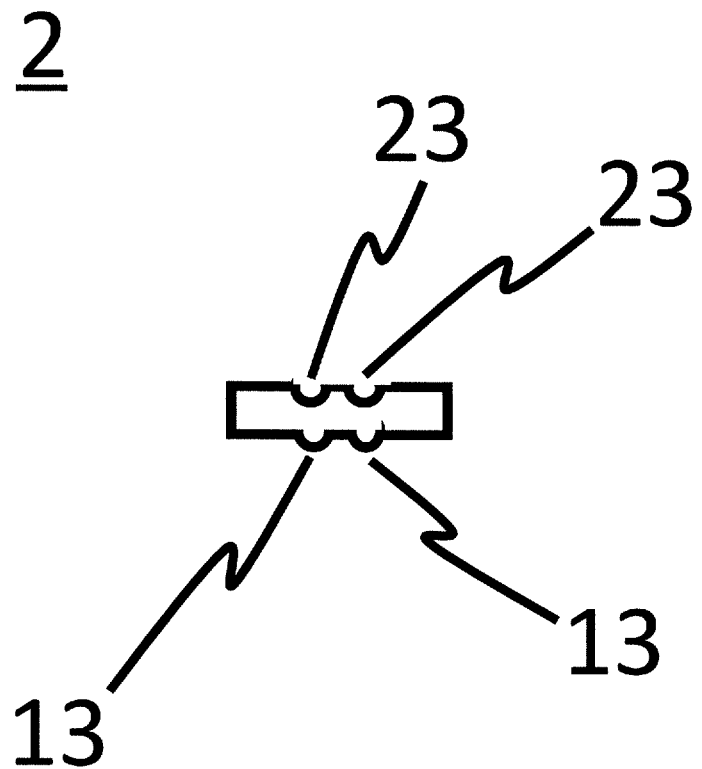
FIG. 14 shows the cross section of the second band portion of the organ stump treatment tool in FIG. 11.
Figure 15:
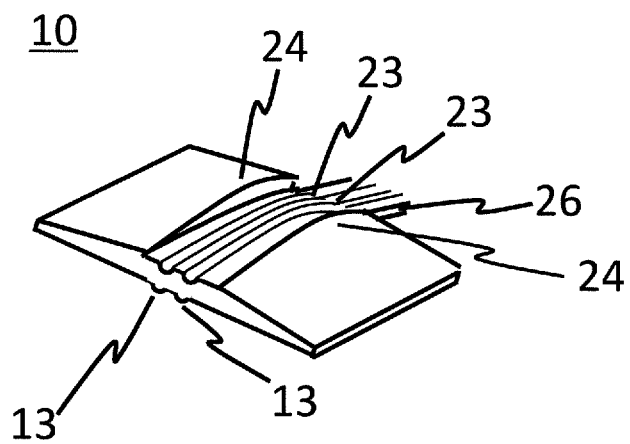
FIG. 15 is a perspective view showing the tongue part of the organ stump treatment tool in FIG. 11.
Figure 16:
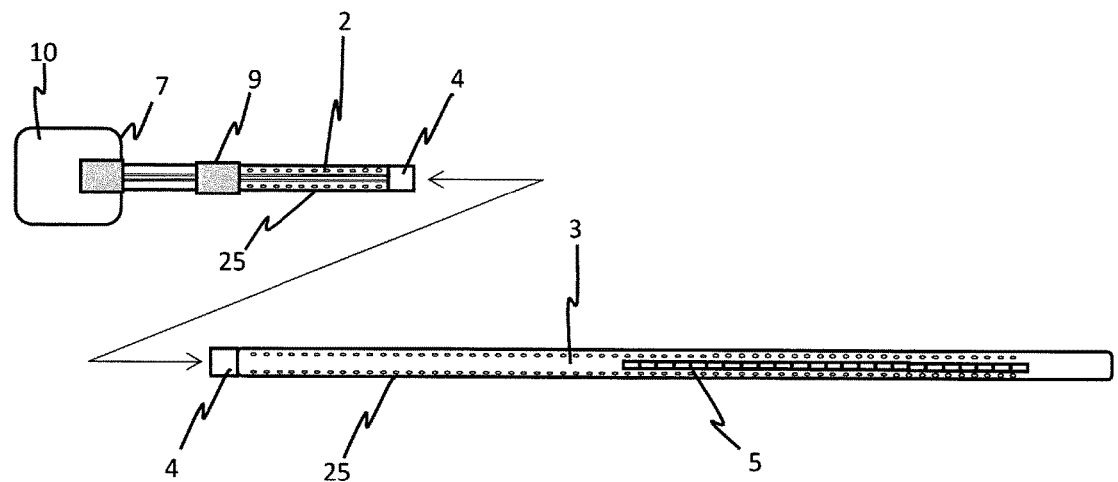
FIG. 16 shows the outer surface of an example of the organ stump treatment tool of the present invention in a developed state.
Figure 17:
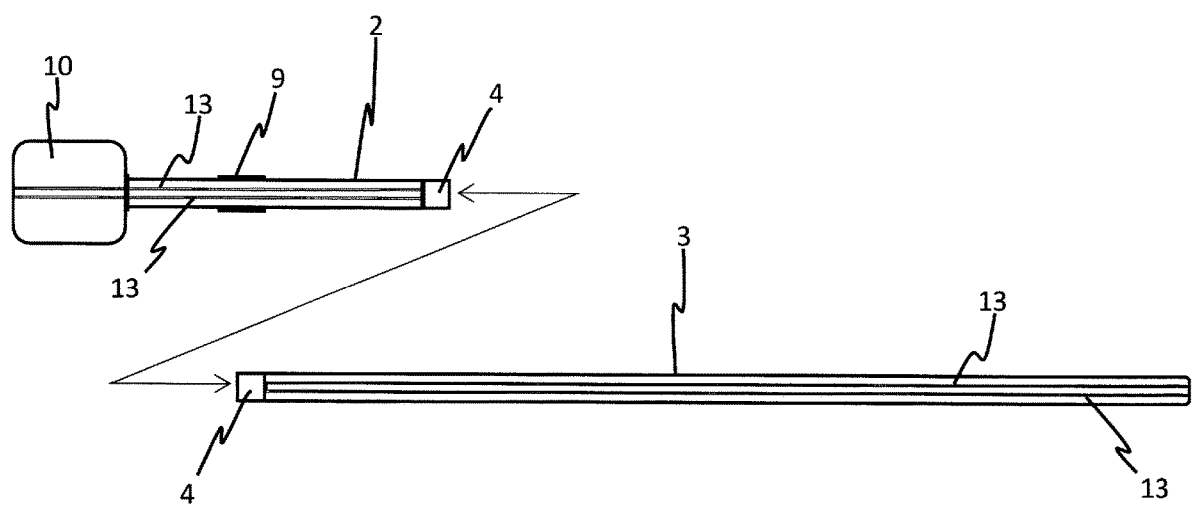
FIG. 17 shows the inner surface of the organ stump treatment tool in FIG. 16 in a developed state.
Figure 18:
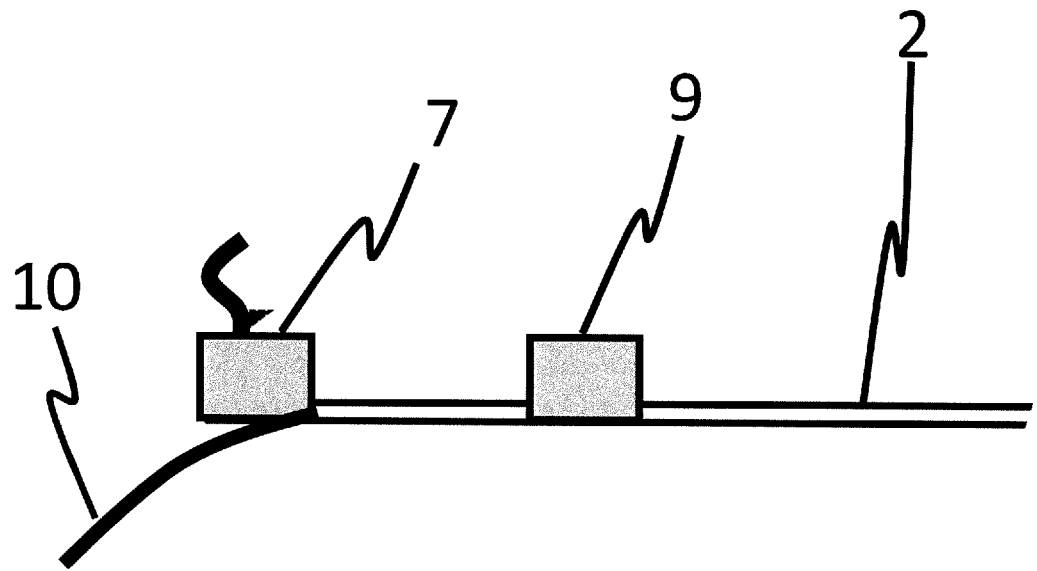
FIG. 18 shows side surfaces of a tongue part and a second band portion of the organ stump treatment tool in FIG. 16.
Figure 19:
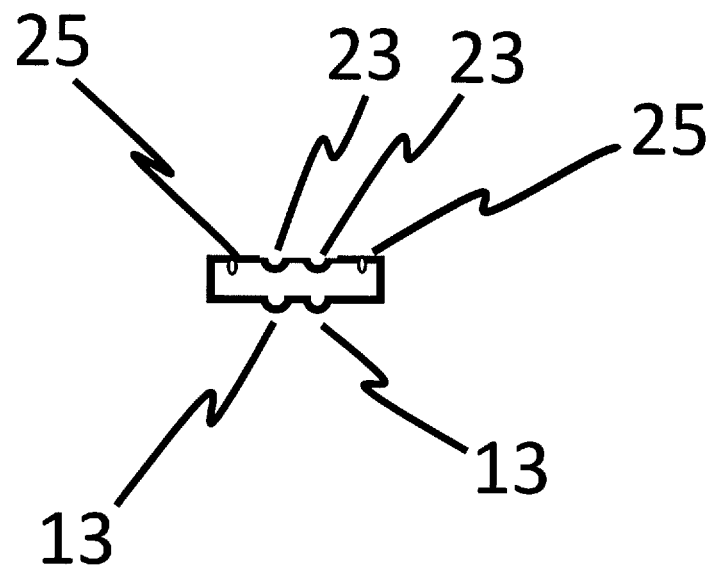
FIG. 19 shows the cross section of the second band portion of the organ stump treatment tool in FIG. 16.

A tongue part 10 is formed in the vicinity of the first locking portion 7. In the organ stump treatment tool shown in FIG. 1, the tongue part 10 is arranged so as to extend in a fan-like shape or a lion mane-like shape along the edge of inner face from the left end to the right end across the distal end of the first locking portion 7 (FIGS. 2 to 4). In an organ stump treatment tool shown in FIG. 11, the tongue part 10 is arranged at the edge of inner face of the distal end of the first locking portion 7 through an attachment base so as to extend toward the distal side (FIGS. 11 to 13). Alternatively, the tongue part may be arranged at the edge of inner face of the first locking portion on the proximal side or the inner surface of the second band portion on the distal end side in such a manner that a main surface of the tongue part extends toward the distal side parallel to the inner surface of the first locking portion (FIGS. 16 to 18). The tongue part 10 is arranged in such a manner that the inner surface of the tongue part 10 is connected smoothly in a non-angular pattern to the inner surface of the distal end of the band portion 2. When the first band portion 3 is inserted into the first locking portion 7 and tightened, the presence of the tongue part 10 makes it possible to prevent an organ tissue from getting caught in the organ stump treatment tool. The tongue part 10 is preferably made of a biodegradable and bioabsorbable polymer.

Figure 5:
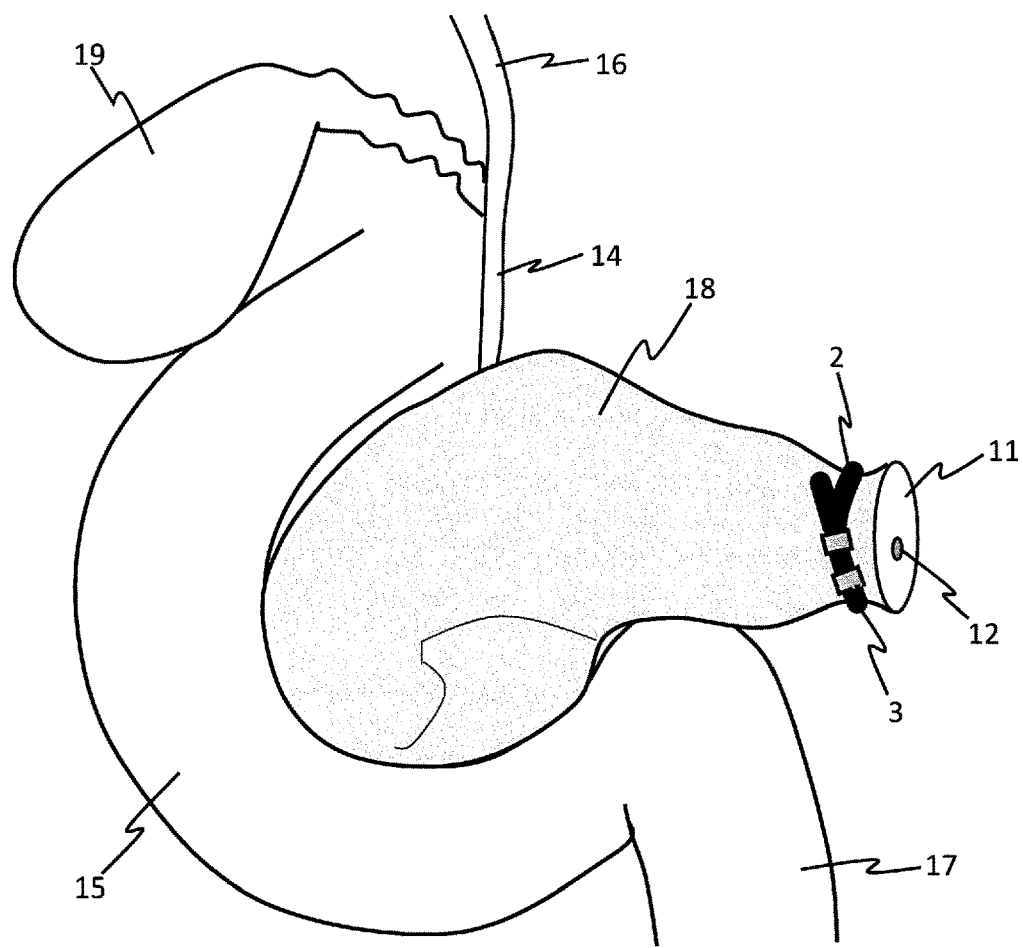
FIG. 5 shows an example of a state in which the organ stump treatment tool of the present invention is attached so as to narrow a pancreatic stump after implementation of pancreatic body and tail resection.

As shown in FIG. 2, at least one ratchet tooth 5 is formed at the outer surface of the first band portion 3. A ratchet is one of mechanisms for limiting an operating direction to one direction. The ratchet tooth 5 can be meshed with the first ratchet pawl 6 at the first locking portion 7. Meshing the ratchet tooth and the first ratchet pawl forms a flattened ring, and an organ 18 (FIG. 5) can be bound tightly and a duct or lumen 12 that opens at a stump 11 of the organ 18 can be ligated with the ring. Tension can be adjusted easily during the binding and ligation (see FIGS. 5 and 6).

In the organ stump treatment tool 1 shown in FIG. 1, the first ratchet pawl 6 is supported in a pivotal manner on the casing of the first locking portion 7. Alternatively, the first ratchet pawl 6 may be fixed in a manner preventing pivotal movement, like a second ratchet pawl.

If the first ratchet pawl 6 is supported in a pivotal manner, the first ratchet pawl 6 can be meshed with the ratchet tooth 5 in a state indicated by a solid line in FIG. 1 or 6 to allow operation only in a direction of contracting a ring formed with the first band portion 3 and the second band portion 2. In a state indicated by dashed lines in FIG. 1 or 6, the ratchet tooth 5 is released from the meshing engagement with the first ratchet pawl 6. Thus, the contraction with the first band portion 3 and the second band portion 2 can be loosened.

Figure 8:
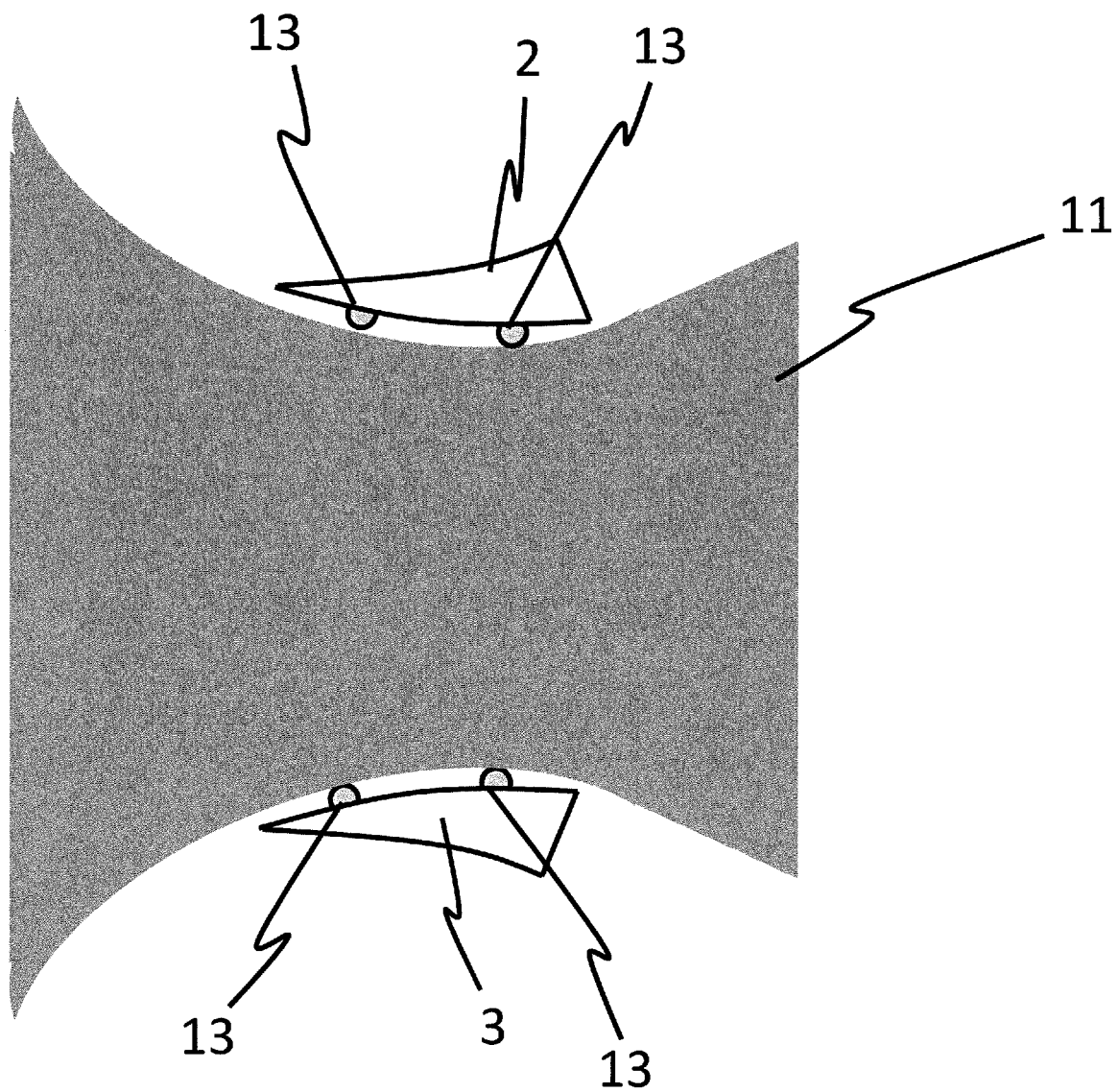
FIG. 8 is a cross-sectional view showing an example of a state in which the organ stump treatment tool of the present invention is attached to a pancreatic stump.
Figure 9:
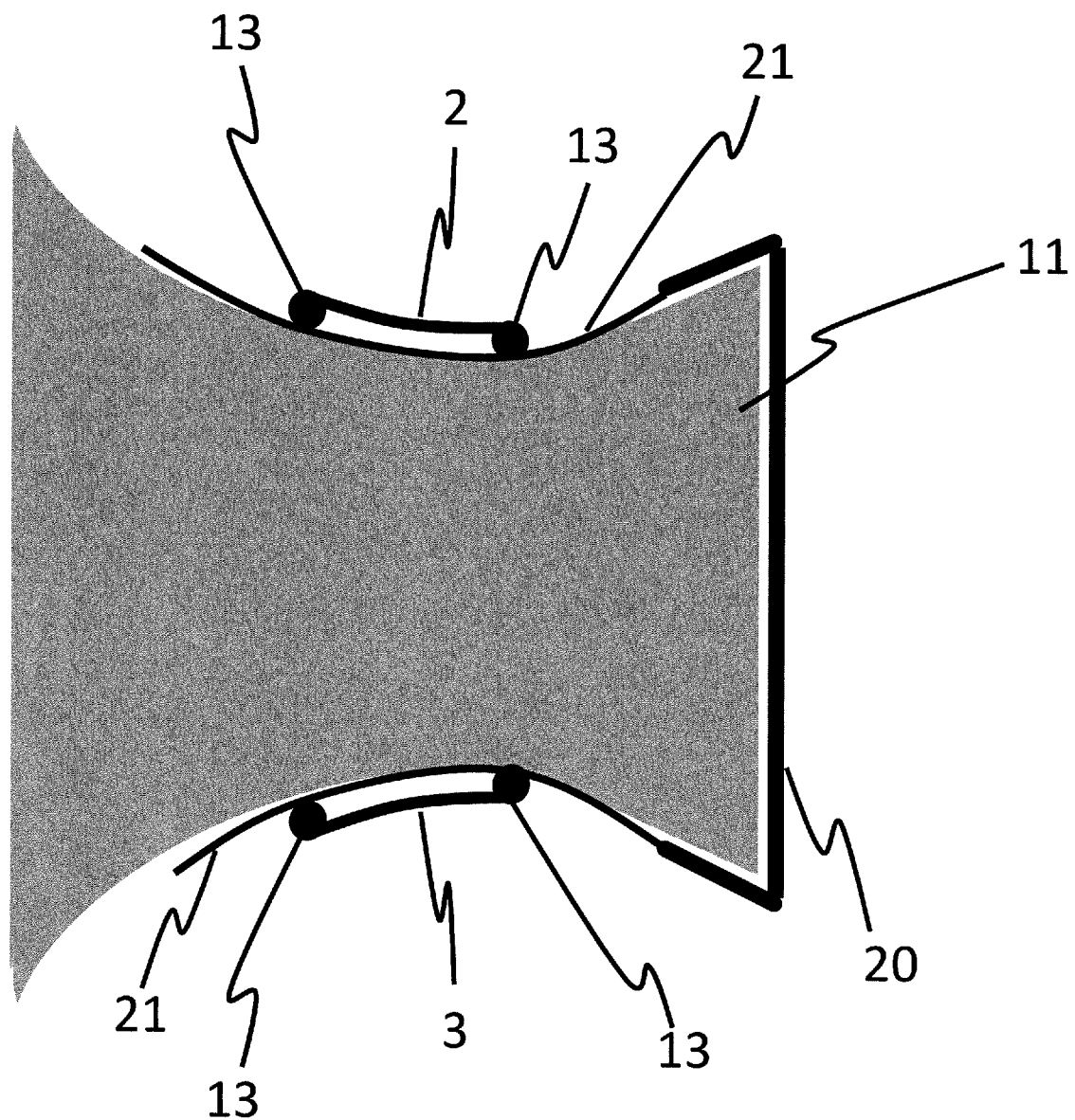
FIG. 9 is a cross-sectional view showing another example of a state in which the organ stump treatment tool of the present invention is attached to a pancreatic stump.

The first band portion and the second band portion comprise at least one convex strip formed at the inner surface of at least one of the first band portion and the second band portion to extend in a lengthwise direction. As shown in FIG. 3, two convex strips 13 are formed continuously in the lengthwise direction at the inner surfaces of the first band portion and the second band portion. As shown in FIG. 8, these convex strips 13 increase frictional force when an organ is bound, thereby contributing to preventing effect from falling off. One convex strip or a plurality of parallel convex strips may be formed in a predetermined range to extend continuously in a longitudinal direction. Alternatively, a plurality of short convex strips (line of short convex strips) may be formed in series spaced at intervals in the longitudinal direction. As shown in FIG. 9, the convex strips 13 may be formed at the edges of the first band portion 3 and the second band portion 2 so as to bulge inwardly. The convex strip is a member capable for preventing side-to-side slippage of the band. While the convex strip is illustrated in the drawings, the shape of the member capable for preventing side-to-side slippage is not limited. The convex strip can be replaced with a line of projections, a concave strip, or a line of concaves, for example.

As shown in FIG. 1, if necessary, the organ stump treatment tool 1 of the present invention can further comprise a second locking portion 9 with a second ratchet pawl 8 made of a biodegradable and bioabsorbable polymer. The second ratchet pawl 8 is fixed in a manner preventing pivotal movement to a casing of the second locking portion 9, so that the ratchet tooth 5 cannot be released from the meshing engagement with the second ratchet pawl 8. The second ratchet pawl 8 can be used for preventing the organ stump treatment tool 1 remaining in an abdominal cavity after surgery from falling off an organ due to loosening of the ratchet.

Another embodiment of the organ stump treatment tool of the present invention is the same as the organ stump treatment tool shown in FIG. 1, except that a concave strip 23 is formed at the outer surfaces of the tongue part 10 and the second band portion 2 and a terrace part 24 is formed at the tongue part 10 (FIGS. 11 to 15).

The concave strip 23 is arranged in such a manner that, when the first interlocking part and the second interlocking part are meshed with each other, a non-slip convex strip formed at the inner surface of the first band portion is fitted in the concave strip 23. In this way, the meshing engagement is stabilized. Side-to-side slippage can be suppressed by fitting the first band portion between at least right and left terrace parts 24 in a pair. As long as a convex strip and a concave strip are configured to be fitted to each other, they can be arranged at reversed positions or can be replaced with a combination of shapes to achieve substantially the same effect, for example. Alternatively, a plurality of convex strips can be fitted in a wide single concave strip.

Figure 10:
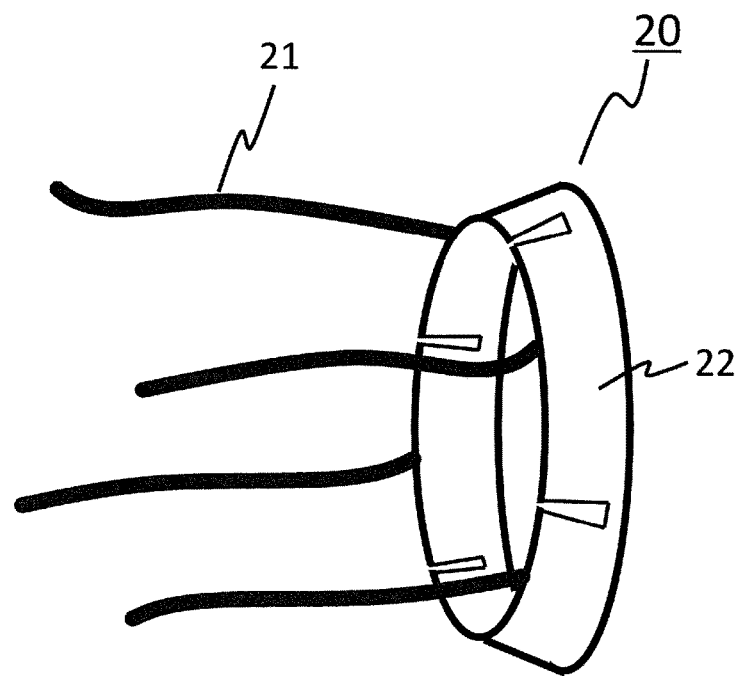
FIG. 10 shows an example of a covering member.
Figure 20:
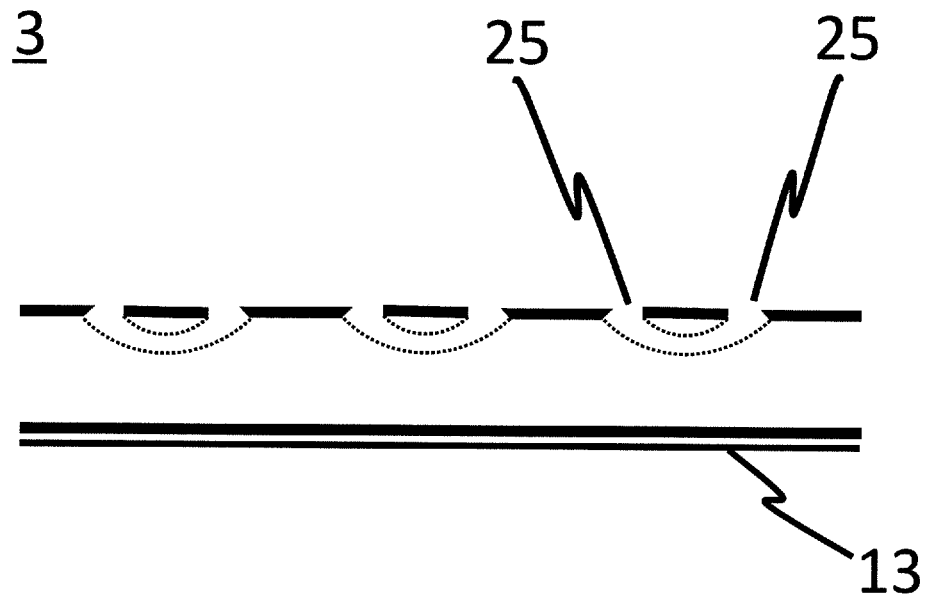
FIG. 20 is an enlarged transparent view of a first band portion of the organ stump treatment tool in FIG. 16 taken from a lateral side.
Figure 21:
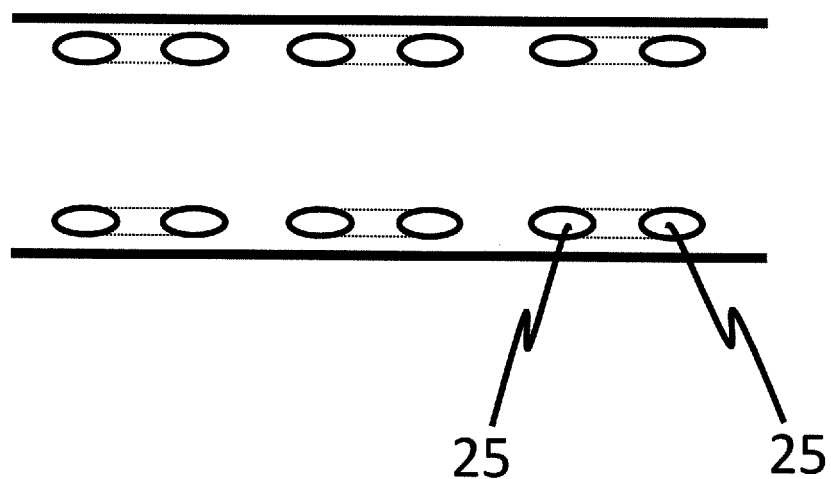
FIG. 21 is an enlarged transparent view of the first band portion of the organ stump treatment tool in FIG. 16 taken from an outer side.

Another embodiment of the organ stump treatment tool of the present invention is the same as the organ stump treatment tool shown in FIG. 1, except that holes (also called eyelet holes in some cases) 25 with openings arranged at least in a line in a lengthwise direction are formed at the first band portion or the second band portion, and the tongue part 10 is replaced with the one shown in FIG. 10 (FIG. 16). As shown in FIGS. 20 and 21, regarding the holes 25, two openings adjacent in a lengthwise direction communicate with each other to form a U-shaped cavity, for example. A digestive tract or a tissue can be sutured to a stump of a digestive organ or a covering member 20 can be supported by passing a thread through the holes 25. In the organ stump treatment tool shown in FIG. 16, the width of the ratchet tooth 5 is reduced for the provision of the holes 25. However, it can be understood that this still achieves substantially equal effect in terms of meshing engagement.

Figure 22:
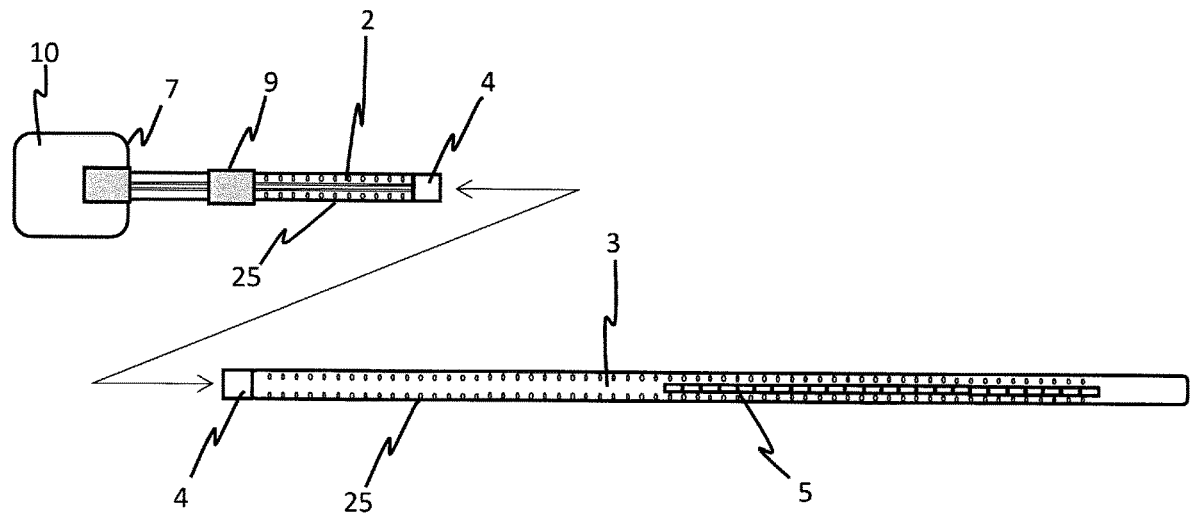
FIG. 22 shows the outer surface of an example of the organ stump treatment tool of the present invention in a developed state.
Figure 23:
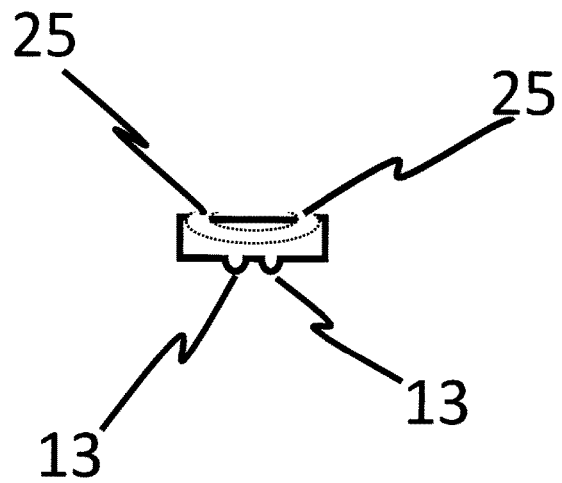
FIG. 23 shows the cross section of a first band portion of the organ stump treatment tool in FIG. 22.
Figure 24:
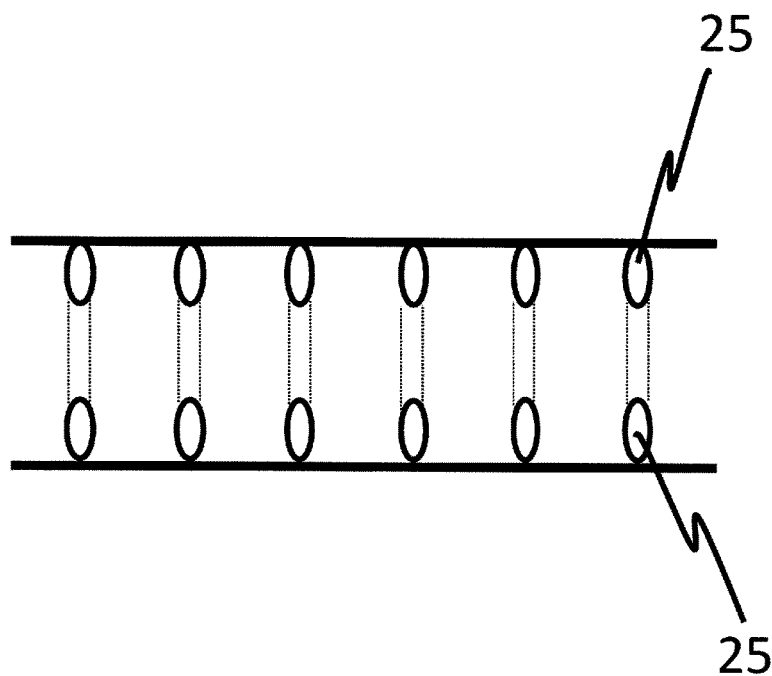
FIG. 24 is an enlarged transparent view of holes arranged at the first band portion of the organ stump treatment tool in FIG. 22 taken from an outer side.
Figure 25:
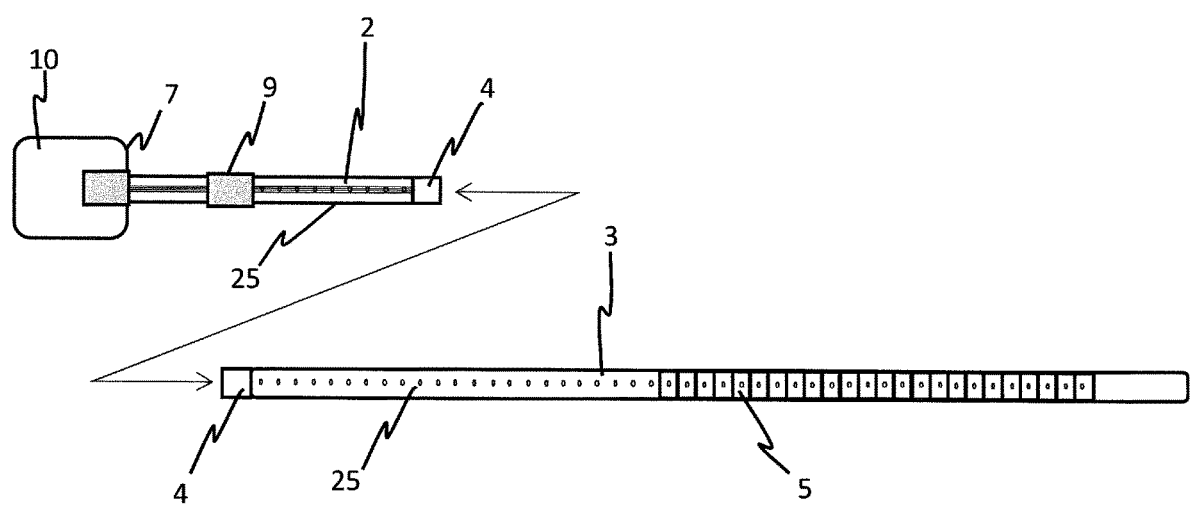
FIG. 25 shows the outer surface of an example of the organ stump treatment tool of the present invention in a developed state.
Figure 26:
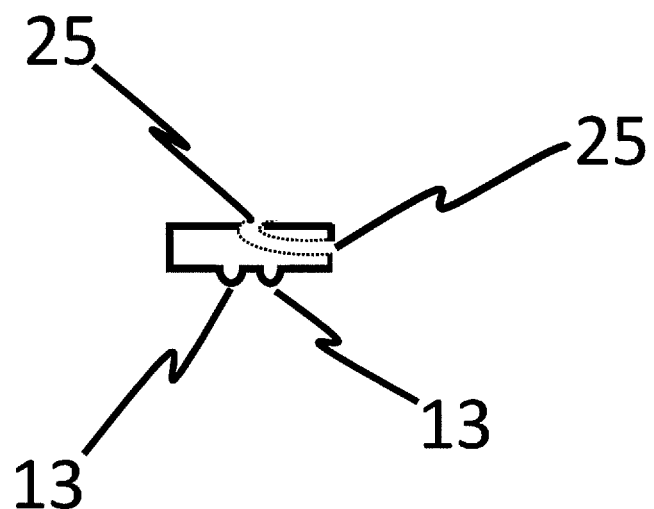
FIG. 26 shows the cross section of the first band portion of the organ stump treatment tool in FIG. 16.
Figure 27:
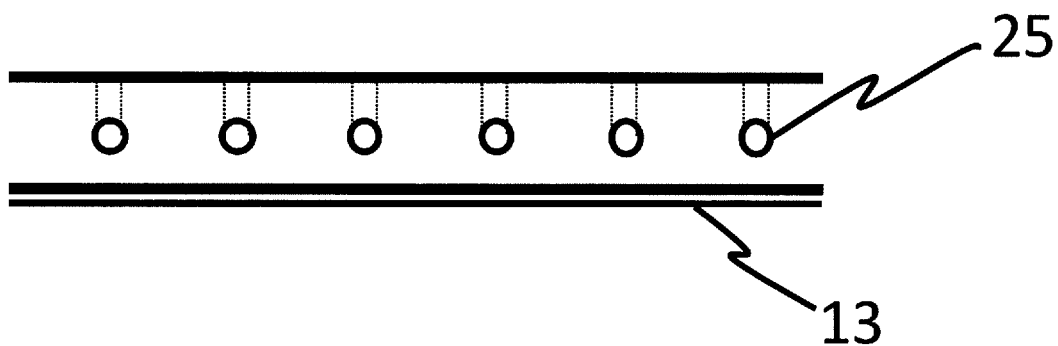
FIG. 27 is an enlarged transparent view of holes arranged at the first band portion of the organ stump treatment tool in FIG. 16 taken from a lateral side.
Figure 28:
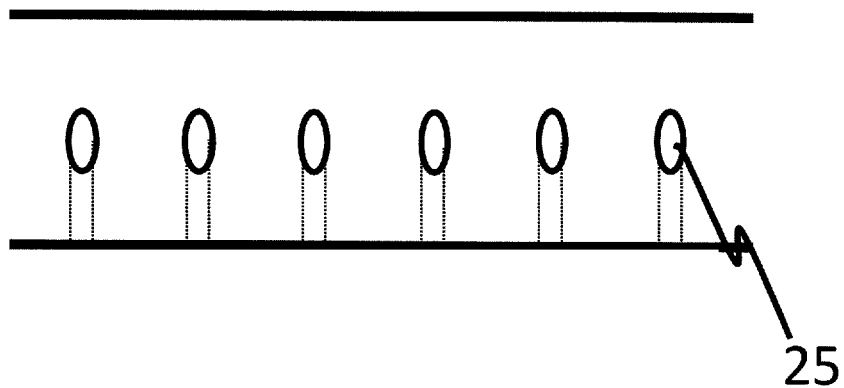
FIG. 28 is an enlarged transparent view of the holes arranged at the first band portion of the organ stump treatment tool in FIG. 16 taken from an outer side.

The holes 25 may be cavities penetrating the band portion from the outer surface to the inner surface. Alternatively, as shown in FIGS. 22 to 24, two openings adjacent in a width direction may be communicated with each other to form a U-shaped cavity. Alternatively, as shown in FIGS. 25 to 28, cavities penetrating the band portion from the outer surface to a side surface may be formed. The cavities in FIGS. 27 and 28 penetrate the band portion from the outer surface to only one of side surfaces. These cavities may be replaced with cavities penetrating the band portion from the outer surface to the both side surfaces alternately, or may be replaced with cavities each penetrating the band portion from the outer surface to the both side surfaces. While the penetrating cavities in FIGS. 23 and 24 are arranged at a substantially right angle to the longitudinal direction of the band portion, they may be arranged obliquely to the longitudinal direction of the band portion.

The organ stump treatment tool of the present invention can further comprise the covering member 20 made of a biodegradable and bioabsorbable polymer. FIG. 10 shows an example of the covering member. While leakage of pancreatic juice is substantially prevented by ligation with the band portion, the covering member 20 may be press-fitted to a stump as shown in FIG. 9 to prevent leakage of the pancreatic juice more reliably. The covering member 20 shown in FIG. 10 comprises a flattened circular sheet having a similar shape to a pancreatic stump, and four bank parts rising from an edge of the sheet. The four bank parts are tilted so as to be reduced in diameter toward the left of the drawing. Garter bands 21 are further provided. As shown in FIG. 9, for example, the garter bands 21 are caught between the first band portion 3, the second band portion 2, and an organ to prevent the covering member 20 from coming off the organ. Asperities may be formed at the outer surface or the inner surface of the garter band 21 for increasing frictional force. The garter band may be a member other than that shown in the drawings. For example, a garter band with a hanging ring allowing the band portion to pass through is applicable. Another applicable garter band has a part such as a hook with which the garter band can be hooked on the band portion. The garter band is preferably made of a biodegradable and bioabsorbable polymer.

Figure 29:
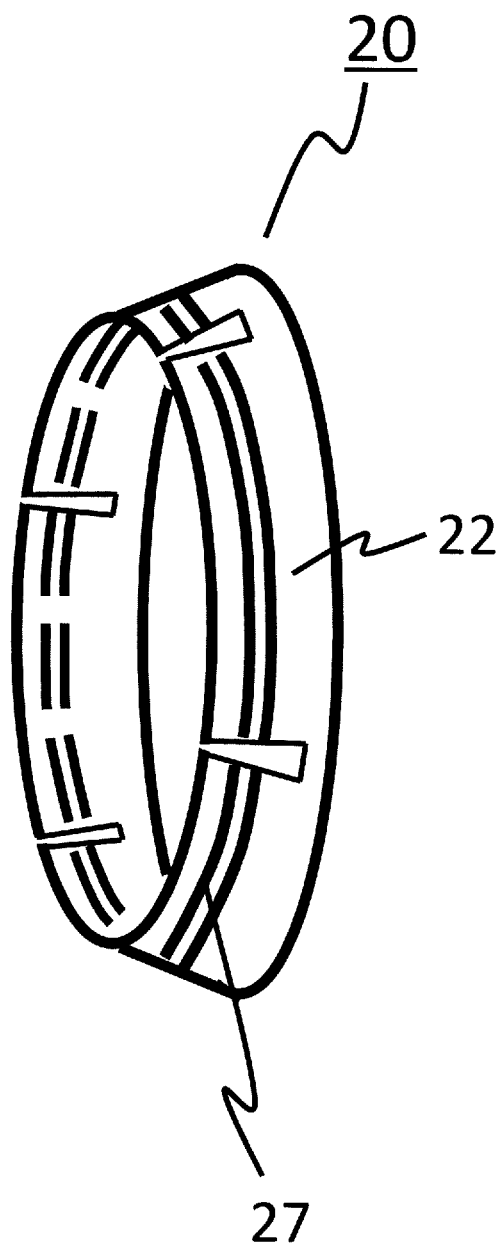
FIG. 29 shows another example of the covering member.
Figure 30:
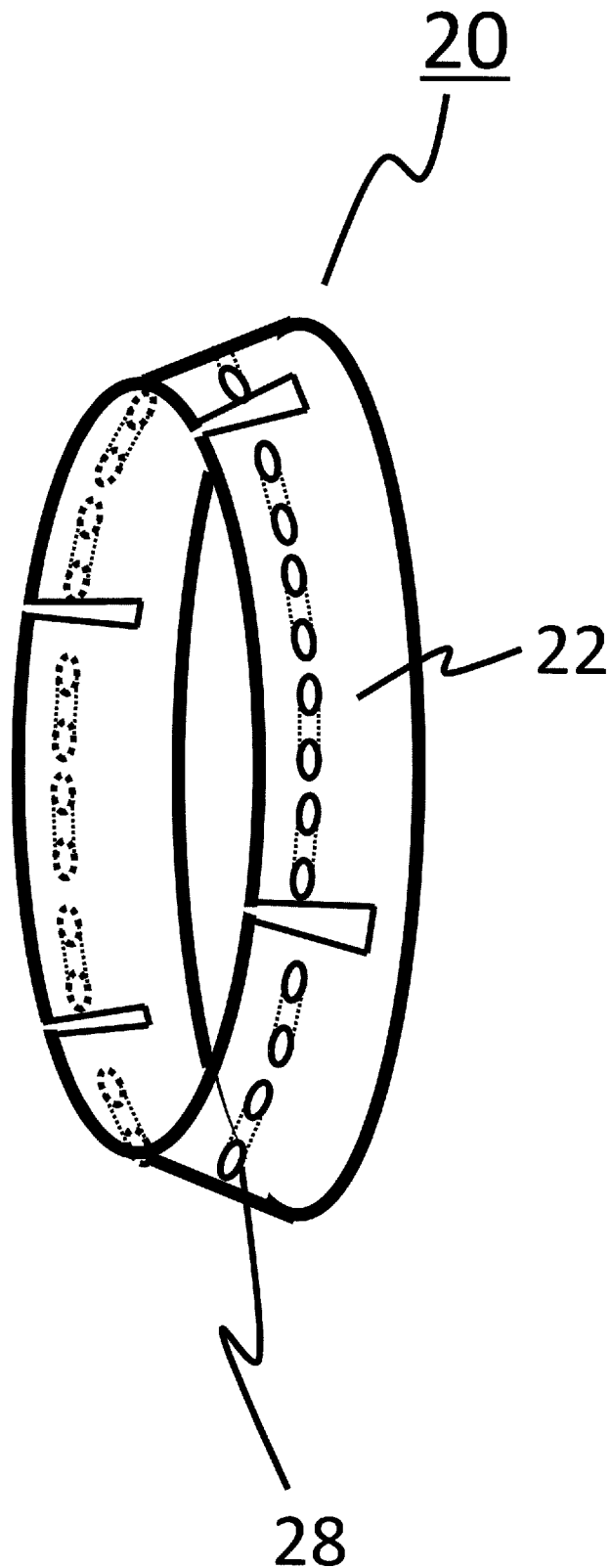
FIG. 30 shows another example of the covering member.
Figure 31:
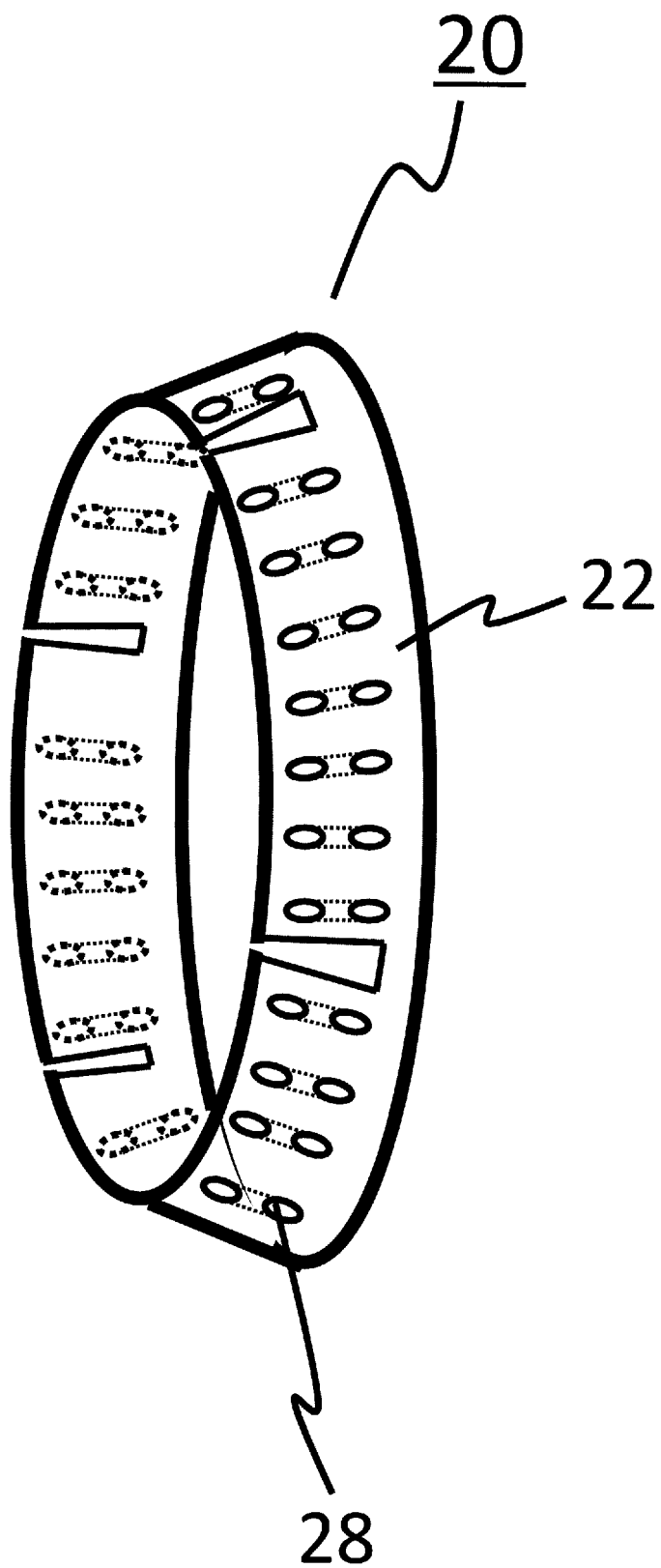
FIG. 31 shows another example of the covering member.

The covering member is not limited to the embodiment shown in FIG. 10. For example, the covering member 20 shown in FIG. 29 comprises a groove 27 at an outer periphery instead of a garter band. The covering member can be fastened to a stump by fitting a linear member such as a thread or a belt into the groove 27. A covering member shown in each of FIGS. 30 and 31 comprises holes instead of a garter band having openings aligned along an outer periphery. The holes form a continuous U-shaped cavity. In the covering member shown in FIG. 30, openings are arranged in a line along the outer periphery. Two adjacent openings form a pair and form a continuous cavity. In the covering member shown in FIG. 31, openings are arranged in two lines along the outer periphery. One opening in one line and one opening in the other line form a pair and form a continuous cavity. In the covering member shown in FIG. 31, holes 28 are arranged in such a manner that a continuous cavity is placed at a substantially right angle to the direction of the outer periphery. Alternatively, the cavity may be placed obliquely to the direction of the outer periphery. The covering member and the band portion can be tied together securely by passing a thread, for example, through the holes 28 at the covering member and the eyelet holes 25 at the band portion.

The covering member may be prepared in advance before surgery so as to conform to the size or shape of a pancreatic stump to be formed by resection estimated through imaging test such as CT, MRI, or abdominal ultrasonography, or may be prepared by in-situ forming. For example, the in-situ forming can be conducted by applying a coating material obtained by dissolving a biodegradable and bioabsorbable polymer in a biocompatible organic solvent to an organ stump, and then removing the organic solvent. Alternatively, the in-situ forming can be conducted by applying a coating material containing a monomer or a prepolymer forming a biodegradable and bioabsorbable polymer and a substance to cause synthetic reaction such as a photopolymerization initiator or a photo-acid-generating agent to an organ stump, and then irradiating the coated film with light.

The organ stump treatment tool of the present invention is not limited to the embodiments shown in the drawings. Modifications resulting from change in the shape, size, color, or material of each of the foregoing members, or modifications resulting from addition of well-known or commonly-used parts other than the foregoing members such as the band portion and the locking portion, are also covered by the technical scope of the present invention.

REFERENCE SIGNS LIST

1: Organ stump treatment tool
2: Second band portion
3: First band portion
4: Joint
5: Ratchet tooth
6: First ratchet pawl
7: First locking portion
8: Second ratchet pawl
9: Second locking portion
10: Tongue part
11: Pancreatic stump
12: Pancreatic duct opening
13: Convex strip
14: Common bile duct
15: Duodenum
16: Common hepatic duct
17: Jejunum
18: Pancreas
19: Gallbladder
20: Covering member
21: Garter band
22: Bank part
23: Concave strip
24: Terrace part
25: Eyelet hole
26: Attachment base
27: Groove
28: Hole

The invention claimed is:

1. An organ stump treatment tool comprising:
an elongated flexible band portion having a distal end and a proximal end, wherein the elongated flexible band portion is flexible from the proximal end to the distal end, and
a locking portion comprising a second interlocking part, wherein the locking portion is at the distal end of the band portion, and the band portion comprises a flexed part between the distal end and the proximal end, and comprises a first interlocking part between the flexed part and the proximal end for meshing engagement with the second interlocking part, wherein the flexed part is a part inflected to be recessed inwardly and is maintained in the inflected shape, whereby the meshing engagement of the first interlocking part with the second interlocking part makes a flattened ring with the flexed part recessed inwardly in, and the flattened ring being configured to bind an organ tightly to ligate a duct or lumen that opens at a stump of the organ.

2. The organ stump treatment tool according to claim 1, further comprising a covering member.

3. The organ stump treatment tool according to claim 2, wherein the covering member is made of a biodegradable and bioabsorbable polymer.

4. The organ stump treatment tool according to claim 1, wherein the elongated flexible band portion is made of a biodegradable and bioabsorbable polymer, and the locking portion comprising the second interlocking part is made of a biodegradable and bioabsorbable polymer.

5. The organ stump treatment tool according to claim 1, wherein the locking portion is on the outer surface of the band portion.

6. An organ stump treatment tool comprising:
an elongated flexible first band portion having a distal end and a proximal end;
an elongated flexible second band portion having a distal end and a proximal end; and
a first locking portion comprising a first ratchet pawl, wherein the first locking portion is at the distal end of the second band portion,
the distal end of the first band portion and the proximal end of the second band portion are joined so as to form a flexed part which is a part inflected to be recessed inwardly and is maintained in the inflected shape, and
at least one ratchet tooth capable of being meshed with the first ratchet pawl is on an outer surface of the first band portion,
whereby meshing engagement of the at least one ratchet tooth with the first ratchet pawl makes a flattened ring with the flexed part recessed inwardly in, and the flattened ring being configured to bind an organ tightly to ligate a duct or lumen that opens at a stump of the organ.

7. The organ stump treatment tool according to claim 6, wherein at least one of the first band portion and the second band portion has an inner surface where at least one convex strip is formed to extend in a lengthwise direction.

8. The organ stump treatment tool according to claim 6, further comprising a tongue part, in the vicinity of the first locking portion, for preventing an organ tissue from getting caught in the organ stump treatment tool.

9. The organ stump treatment tool according to claim 6, wherein the distal end of the first band portion and the proximal end of the second band portion are joined at an angle smaller than a right angle so as to define a nonangular and smooth inner surface.

10. The organ stump treatment tool according to claim 6, further comprising a second locking portion comprising a second ratchet pawl, wherein
the first ratchet pawl is configured to be allowed to be released from meshing engagement with the at least one ratchet tooth meshed with the first ratchet pawl, and the second ratchet pawl is configured to be prohibited from being released from meshing engagement with the at least one ratchet tooth once meshed with the second ratchet pawl.

11. The organ stump treatment tool according to claim 10, wherein the second locking portion is made of a biodegradable and bioabsorbable polymer.

12. The organ stump treatment tool according to claim 6, wherein the first band portion or the second band portion comprises holes having openings aligned in a lengthwise direction.

13. The organ stump treatment tool according to claim 6, wherein the elongated flexible first band portion is made of a biodegradable and bioabsorbable polymer, the elongated flexible second band portion is made of a biodegradable and bioabsorbable polymer, and the first locking portion is made of a biodegradable and bioabsorbable polymer.

14. An organ stump treatment tool comprising:
an elongated flexible first band portion having a distal end and a proximal end;
an elongated flexible second band portion having a distal end and a proximal end; and
a first locking portion comprising a first ratchet pawl, wherein the first locking portion is at the distal end of the second band portion,
the distal end of the first band portion and the proximal end of the second band portion are joined so as to flex the first band portion and the second band portion, and
at least one ratchet tooth capable of being meshed with the first ratchet pawl is on an outer surface of the first band portion,
whereby meshing engagement of the at least one ratchet tooth with the first ratchet pawl makes a flattened ring which there is a flexed part recessed inwardly in, and the flattened ring being configured to bind an organ tightly to ligate a duct or lumen that opens at a stump of the organ, wherein at least one of the first band portion and the second band portion has an inner surface where at least one convex strip is formed to extend in a lengthwise direction.

15. An organ stump treatment tool comprising:
an elongated flexible first band portion having a distal end and a proximal end;
an elongated flexible second band portion having a distal end and a proximal end; and
a first locking portion comprising a first ratchet pawl, wherein the first locking portion is at the distal end of the second band portion,
the distal end of the first band portion and the proximal end of the second band portion are joined so as to flex the first band portion and the second band portion, and
at least one ratchet tooth capable of being meshed with the first ratchet pawl is on an outer surface of the first band portion,
whereby meshing engagement of the at least one ratchet tooth with the first ratchet pawl makes a flattened ring which there is a flexed part recessed inwardly in, and the flattened ring being configured to bind an organ tightly to ligate a duct or lumen that opens at a stump of the organ, and
the organ stump treatment tool further comprising a second locking portion comprising a second ratchet pawl, wherein
the first ratchet pawl is configured to be allowed to be released from meshing engagement with the at least one ratchet tooth meshed with the first ratchet pawl, and the second ratchet pawl is configured to be prohibited from being released from meshing engagement with the at least one ratchet tooth once meshed with the second ratchet pawl.

16. The organ stump treatment tool according to claim 15, wherein the second locking portion is made of a biodegradable and bioabsorbable polymer.

17. An organ stump treatment tool comprising:
an elongated flexible first band portion having a distal end and a proximal end;
an elongated flexible second band portion having a distal end and a proximal end; and
a first locking portion comprising a first ratchet pawl, wherein the first locking portion is at the distal end of the second band portion,
the distal end of the first band portion and the proximal end of the second band portion are joined so as to flex the first band portion and the second band portion, and
at least one ratchet tooth capable of being meshed with the first ratchet pawl is on an outer surface of the first band portion,
whereby meshing engagement of the at least one ratchet tooth with the first ratchet pawl makes a flattened ring which there is a flexed part recessed inwardly in, and the flattened ring being configured to bind an organ tightly to ligate a duct or lumen that opens at a stump of the organ, wherein the first band portion or the second band portion comprises holes having openings aligned in a lengthwise direction.

* * * * *